United States Patent
Klvana et al.

(10) Patent No.: US 9,920,021 B2
(45) Date of Patent: Mar. 20, 2018

(54) METHOD OF PREPARING VORTIOXETINE

(71) Applicant: Zentiva k.s., Prague (CZ)

(72) Inventors: Robert Klvana, Prague (CZ); Stanislav Radl, Kvetnice (CZ); Jindrich Richter, Pardubice (CZ)

(73) Assignee: Zentiva k.s., Prague (CZ)

( * ) Notice: Subject to any disclaimer, the term of this patent is extended or adjusted under 35 U.S.C. 154(b) by 0 days.

(21) Appl. No.: 15/324,712

(22) PCT Filed: Jul. 8, 2015

(86) PCT No.: PCT/CZ2015/000071
§ 371 (c)(1),
(2) Date: Jan. 8, 2017

(87) PCT Pub. No.: WO2016/004908
PCT Pub. Date: Jan. 14, 2016

(65) Prior Publication Data
US 2017/0204074 A1     Jul. 20, 2017

(30) Foreign Application Priority Data
Jul. 8, 2014   (CZ) ..................... 2014-471

(51) Int. Cl.
C07D 211/20   (2006.01)
C07D 211/70   (2006.01)
C07D 295/096  (2006.01)
C07C 323/00   (2006.01)

(52) U.S. Cl.
CPC ........ C07D 295/096 (2013.01); C07C 323/00 (2013.01)

(58) Field of Classification Search
CPC .................. C07D 211/20; C07D 211/70
See application file for complete search history.

(56) References Cited

FOREIGN PATENT DOCUMENTS

WO    WO 2003/029232    4/2003
WO    WO 2007/144005    12/2007

OTHER PUBLICATIONS

International Search Report for PCT/CZ2015/000071 dated Sep. 28, 2015.

*Primary Examiner* — Bruck Kifle
(74) *Attorney, Agent, or Firm* — Pearl Cohen Zedek Latzer Baratz LLP

(57) ABSTRACT

The new method of preparing 1-(2-(2,4-di-methylphenyl-sulphanyl)phenyl)piperazine of formula (I) or its salt comprises a reaction of 2-(2,4-dimethylphenyl-sulphanyl)benzeneamine of formula (XI), wherein Me is methyl, with a suitable precursor of formation of piperazine ring of formula (XII), wherein LG is a leaving group and R is hydrogen or a protective group, in a suitable organic solvent, wherein the reaction is carried out without presence of a base in a neutral or acidic environment. (Formulae (I), (XI), (XII))

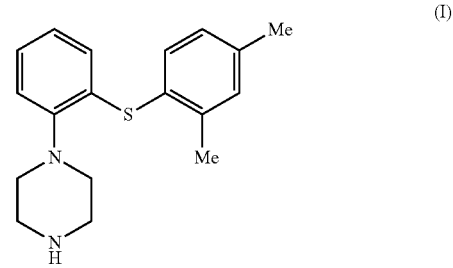

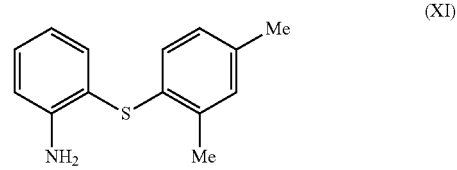

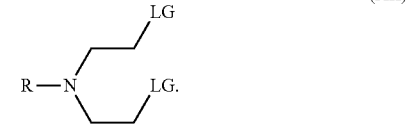

18 Claims, No Drawings

METHOD OF PREPARING VORTIOXETINE

CROSS-REFERENCE TO RELATED APPLICATIONS

This application is a National Phase Application of PCT International Application No. PCT/CZ2015/000071, International Filing Date Jul. 8, 2015, entitled "METHOD OF PREPARING VORTIOXETINE" claiming priority of Czech Patent Application No. PV 014-471, filed Jul. 8, 2014, all of which are hereby incorporated by reference in their entirety.

TECHNICAL FIELD

The invention relates to a new method of preparing 1-[2-(2,4-dimethylphenylsulphanyl)phenyl]piperazine of formula I

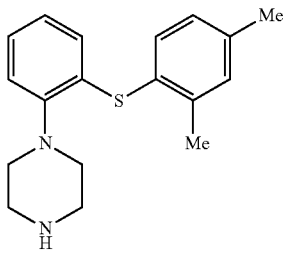

known under the name vortioxetine. Vortioxetine is a modern atypical antidepressant, used in the form of hydrobromide under the trademark Brintellix.

BACKGROUND ART

Basic patent WO 2003029232 describes preparation of vortioxetine of formula I using a reaction in solid phase, wherein piperazine bound to the solid phase reacts with eta(6)-1,2-dichlorobenzene-eta(5)-cyclopentadienyl iron hexafluorophosphate in the presence of potash ($K_2CO_3$) in THF with formation of N,N'-disubstituted piperazine of formula II. This substance is then condensed with the sodium salt of 2,4-dimethylthiophenol of formula III, prepared in situ from the respective thiophenol and NaH. This condensation is carried out photochemically; subsequent cleaving from the solid phase by means of trifluoroacetic acid releases vortioxetine. Total yield of the described reaction is 17% (Scheme 1), purity (UV, ELSD) 95%, 100%.

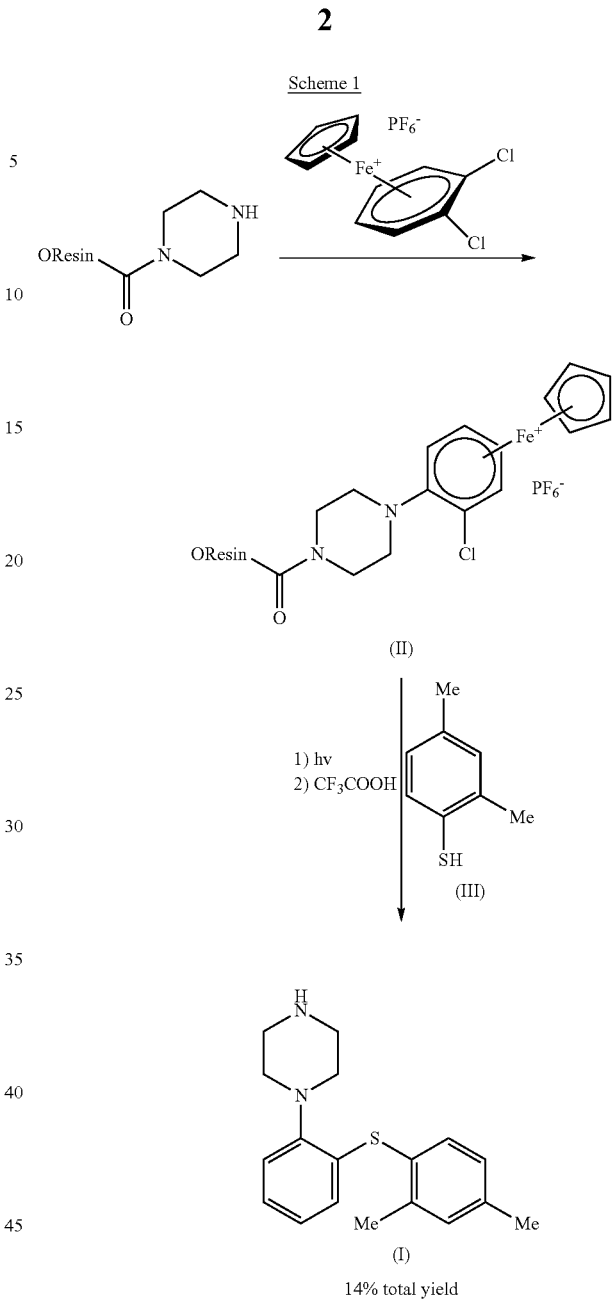

Patent WO 2007/144005 describes a strategy starting from 2-bromoiodobenzene of formula IV and 2,4-dimethylthiophenol of formula III, which, in the presence of suitable catalysts, provide 1-(2-bromophenylsulphanyl)-2,4-dimethylbenzene of formula V. This can also be prepared by coupling of 1-iodo-2,4-dimethylbenzene of formula VIa or 1-bromo-2,4-dimethylbenzene of formula VIb with 2-bromobenzenethiol of formula VII. Arylbromide of formula V is then converted to the vortioxetine base of formula I by the reaction with piperazine in the presence of a suitable catalytic system, typically in the presence of Pd(dba)$_2$, BINAP, and t-BuONa. Piperazine can also be replaced by N-Boc-piperazine, providing the intermediate of formula VII, deprotection of which affords vortioxetine of formula I (Scheme 2).

Scheme 2

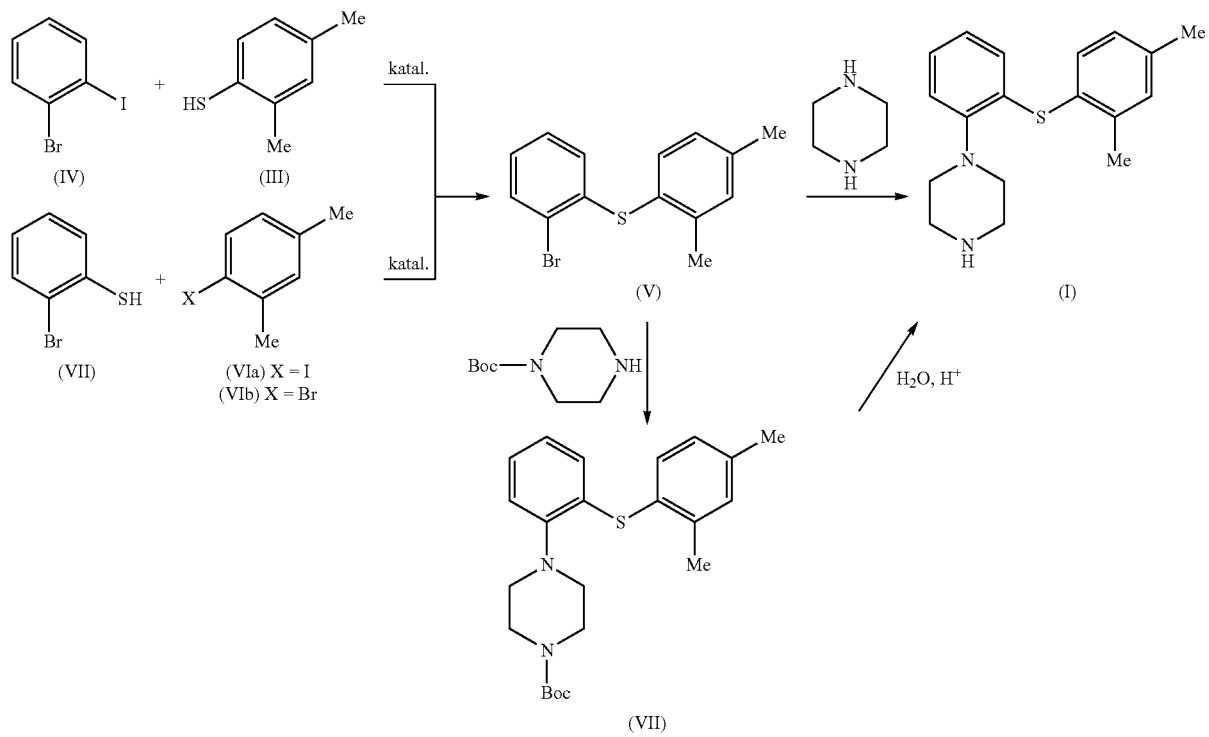

Patent WO 2007/144005 also describes the synthesis of the intermediate of formula VII shown in Scheme 3, consisting in the reaction of 2-bromoiodobenzene of formula IV with N-Boc-piperazine in the presence of a suitable catalytic system, providing an intermediate of formula VIII, further coupling of which with the thiol of formula III provides the intermediate of formula VII.

Scheme 3

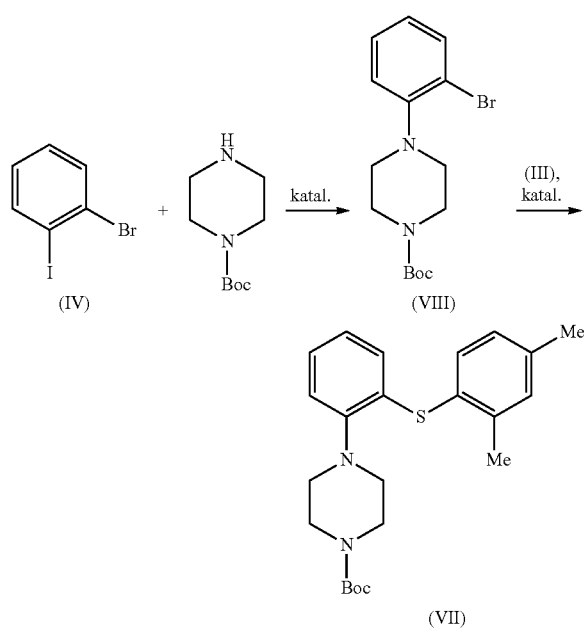

The present invention, relating to a new procedure of preparing vortioxetine of formula I, in comparison with the known state of the art, provides an advantage of preparing vortioxetine of high purity (99.8%) using, in addition, cheap starting substances. Therefore, the proposed procedure is also beneficial from the economical point of view for industrial use and can be simply reproduced.

DISCLOSURE OF INVENTION

The invention provides an improved method of preparing vortioxetine of formula I, comprising the reaction of the thiol of formula III with a suitable 2-nitrohalobenzene of formula IX, preferably with cheap 2-nitrochlorobenzene of formula IXb, in the presence of a base, preferably of sodium hydroxide, with formation of the nitro derivative of formula X. In the next step, the intermediate of formula X is reduced to the amino derivative of formula XI. In the subsequent step, a piperazine ring is built by the reaction with a suitable precursor of formula XII possessing two easily leaving groups (LG), in a suitable solvent, preferably without presence of any base in a neutral or acidic environment. The nitrogen atom in such precursor can be protected with a suitable protective group (PG); in this case, the intermediate of formula XIII, formed by the reaction, is subsequently deprotected and provides vortioxetine of formula I. Precursors of formula XIIb with their nitrogen atom protected with a suitable protective group PG can preferably be compounds having halogenides or sulphonates as LG and COOR' as protective groups, wherein R' is a (un)branched C1-C5 alkyl, preferably ethoxycarbonyl or butyloxycarbonyl (Boc). Suitable precursors with unprotected N atom of formula IIIa can preferably be used, where the reaction directly provides vortioxetine of formula I. Compounds having, as the LG, atoms of Cl, Br, I and groups OMs, OTs have proved preferable, the most preferable being bis-(2-chloroethyl) amine or its salts (Scheme 4).

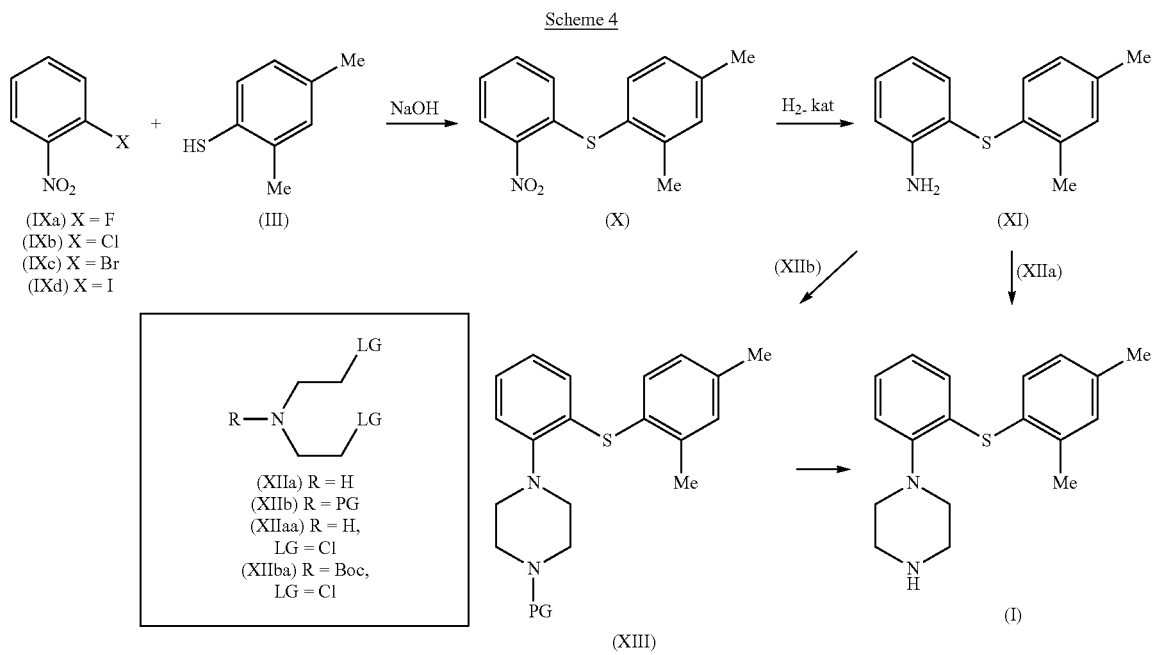

DETAILED DESCRIPTION OF INVENTION

The invention provides an improved method of preparing vortioxetine of formula I, comprising the reaction of the thiol of formula III with a suitable 2-nitrohalobenzene of formula IX, preferably with cheap 2-nitrochlorobenzene of formula IXb, in the presence of a base with formation of the nitro derivative of formula X. Suitable bases include alkali metal alcoholates (for instance, sodium methanolate, potassium methanolate, sodium ethanolate, potassium ethanolate, or potassium tert-butanolate), or alkali hydroxides (for instance, sodium hydroxide, potassium hydroxide, cesium hydroxide, barium hydroxide). Using these bases, it is possible to first prepare the respective salt from the respective thiolate by any of commonly known procedures; the salt can then be used for reaction with the nitro derivative of formula IX, or the salt can be generated in situ using the mentioned bases. Preferably, carbonates or hydrogen carbonates (sodium carbonate, potassium carbonate, cesium carbonate, sodium hydrogen carbonate, potassium hydrogen carbonate) can be used as the bases and the respective salt can be generated in situ in the reaction mixture. The reaction can be carried out without presence of phase transfer catalysts, preferably, however, also in the presence of such compounds, for instance, quaternary ammonium salts (for instance, tetrabutylammonium bromide, tetrabutylammonium hydrogen sulphate), crown ethers (for instance 18-crown-6, 15-crown-5).

The reduction of the nitro derivative (X) to the amino derivative of formula XI can be carried out under conditions known for this classical reaction. Reduction with metals (Fe, Zn, Sn) in an acidic environment using various acids (HCl, $H_2SO_4$, $H_3PO_4$), reduction with metal salts ($SnCl_2$, $FeSO_4$), but also other reducing agents commonly known for this reaction have proved useful for this reaction. Another possibility of carrying out the reduction of the nitro group is catalytic hydrogenation or transfer-hydrogenation on a suitable catalyst (for instance, hydrazine+activated charcoal+$FeCl_3$). Due to the presence of the sulphur atom in the molecule of the intermediate (X), the choice of suitable catalysts is somewhat narrowed. Screening of catalytic hydrogenation and transfer-hydrogenation with using various catalysts based on Pt, Pd, Ni, Fe, or Co on various carriers in a series of solvents has been carried out. The best results have been reached with several batches of commercial catalysts based on Ni in solvents including alcohols, preferably C1-C5 (preferably methanol, ethanol) and C1-C5 esters (preferably ethyl acetate, isopropyl acetate, ethyl propionate).

The subsequent reaction of the amino derivative (XI) with precursors of formation of the piperazine nucleus of formula XII has been tested with several possible compounds of formula XII, including N-unsubstituted derivatives of formula XIIa and the respective N-protected compounds of formula XIIb. The reaction can be carried out in numerous solvents, preferably in aromatic solvents, such as chlorobenzene, xylene, toluene, α,α,α-trifluorotoluene at temperatures ranging between 100 and 140° C., preferably at 103-111° C., using 1-1.2 equivalents of the precursor of formula XII for 1 equivalent of the amino derivative of formula XI. Using 1 to 1.1 equivalents of the precursor of formula XII and carrying out the reaction in the presence of an alkali iodide (LiI, NaI, KI) or $Bu_4NI$ is especially preferable, more preferred in the presence of NaI or KI. The reaction is suitably carried out in a neutral or acidic environment, which leads to reduced content of impurities.

Vortioxetine of formula I can be preferably isolated in the form of suitable salts, for instance, in the form of well crystalline 4-chlorobenzoate or 3,5-dinitrobenzoate, which show good crystallizing and purifying properties, as well as high stability.

The invention is explained in more details in the following working examples. These examples, which elucidate the improvement of the procedure according to the invention, are of an exclusively illustrative character and do not limit the scope of the invention in any respect.

The term room temperature is intended to describe a temperature between 15° C. and 30° C., preferably between 20 and 25° C.

The term brine is intended to describe a saturated solution of sodium chloride.

EXAMPLES

Example 1

Preparation of
2-(2,4-dimethylphenylsulphanyl)nitrobenzene (X)

1-Chloro-2-nitrobenzene of formula IXb, (116 g; 739 mmol) is dissolved in EtOH (550 ml) at room temperature. 2,4-Dimetylthiophenol (100 ml; 739 mmol) and a solution of NaOH (30 g; 750 mmol) in 100 ml of distilled water are added to the solution. The reaction mixture is heated to 50° C. within 1 hour and then this temperature is maintained for additional 4 hours, during which time yellow suspension of the product is separated. After cooling down the suspension to 15° C., the product is filtered and washed with 50 ml of 80% ethanol and 100 ml of 70% ethanol. The yield of the bright yellow product is 191 g (100%). Melting point 85.9-88.0° C. $^1$H NMR (DMSO-$d_6$, 250 MHz) δ 8.25 (d, 1H); 7.51 (m, 2H); 7.35 (m, 2H); 7.18 (d, 1H); 6.67 (d, 1H); 2.36 (s, 3H); 2.23 (s, 3H). HPLC 99.8%.

Example 2

Preparation of
2-(2,4-dimethylphenylsulphanyl)benzeneamine of formula XI 2-(2,4-Dimethylphenylsulphanyl)nitrobenzene of formula X, (5 g; 19.3 mmol) is suspended in ethanol (40 ml). Hydrazine monohydrate (3 ml; 60 mmol) and activated charcoal (80 mg) is added to the suspension. The solution of FeCl$_3$.6H$_2$O (0.2 g; 0.7 mmol) in ethanol (10 ml) is dropwise-added to the stirred suspension at room temperature. The reaction mixture is heated to mild reflux. After 12 hours, the conversion is >98%.

Example 3

Preparation of
2-(2,4-Dimethylphenylsulphanyl)benzeneamine of Formula XI 2-(2,4-Dimethylphenylsulphanyl)nitrobenzene of formula X (25.9 g; 100 mmol) is placed into an autoclave, 250 ml of methanol and 3.9 g of Raney-Ni are added. The mixture is hydrogenated at pressure of 2000 kPa and 50° C. for 2 hours. The reaction mixture is cooled down to 20° C., the catalyst is filtered off, and the filtration cake is washed in 20 ml of methanol. Methanol is evaporated and an oily product is obtained with the yield of 99%; HPLC 99.2%.

Example 4

Preparation of
2-(2,4-dimethylphenylsulphanyl)benzeneamine hydrochloride of Formula XI.(HCl)

2-(2,4-Dimethylphenylsulphanyl)nitrobenzene of formula X (8.0 g; 30.85 mmol) is placed into an autoclave, 80 ml of ethyl acetate and 0.80 g of Pd/C (10%) are added. The mixture is hydrogenated at pressure of 300-400 kPa and 20° C. for 24 h. After filtering off the catalyst and thickening the reaction mixture under reduced pressure, 10 ml of solution of HCl in ethanol and, subsequently, 60 ml of diethyl ether are added. The separated product is filtered off and washed with diethyl ether. 7.73 g of white crystals are obtained (yield 94%), HPLC purity 99.3%.

Example 5

Preparation of
2-(2,4-dimethylphenylsulphanyl)benzeneamine hydrochloride of Formula XI.(HCl)

2-(2,4-Dimethylphenylsulphanyl)nitrobenzene of formula X (5 g; 19.3 mmol) is dissolved in ethyl acetate (40 ml) and Raney-Ni (1 g) is added. The well stirred suspension is hydrogenated at room temperature and hydrogen pressure of 2000 kPa for 20 hours. After filtering off the catalyst, 3M HCl in methyl-tert-butyl ether (MTBE) (10 ml) is added to the filtrate. The separated hydrochloride of the required product is isolated by filtration. Yield 4.3 g (84%); HPLC 99.2%. $^1$H NMR (dimethyl sulfoxide (DMSO-$d_6$, 250 MHz) δ 8.62 (s, 3H); 7.44 (d, 1H); 7.29 (t, 1H); 7.06 (m, 5H); 2.29 (s, 3H); 2.26 (s, 3H).

Example 6

Preparation of
2-(2,4-dimethylphenylsulphanyl)benzeneamine hydrochloride of Formula XI.(HCl)

2-Chloronitrobenzene of formula IXb, (4.5 g; 29 mmol) is dissolved in EtOH (25 ml) at room temperature. 2,4-Dimetylthiophenol of formula III, 4 g; 29 mmol) and a solution of NaOH (1.2 g; 30 mmol) in 2 ml of distilled water are added to the formed solution. The reaction mixture is heated to 50° C. within 1 hour; this temperature is then maintained for additional 4 hours, during which time yellow suspension of the product is separated. Fe powder (10 μm; 4.5 g) and concentrated HCl (0.16 ml) are added to the suspension. The suspension is mildly refluxed under stirring for 12 hours. The formed Fe sludge is filtered off and thoroughly washed with ethanol. The combined filtrates are concentrated, the concentrated product is dissolved in ethyl acetate (40 ml) and concentrated HCl (2.4 ml) is added. The separated hydrochloride is filtered off and well washed with ethyl acetate. 5.2 g of the product is obtained (yield 67%), HPLC 98.5%.

Example 7

Preparation of
2-(2,4-dimethylphenylsulphanyl)benzeneamine hydrochloride of Formula XI.(HCl)

1-Chloro-2-nitrobenzene of formula IXb, (34.8 g; 22.2 mmol) is dissolved in EtOH (165 ml) at room temperature. 2,4-Dimetylthiophenol of formula III, (30 ml; 22 mmol) and a solution of NaOH (9 g; 22.5 mmol) in 16 ml of distilled water are added to the formed solution. The reaction mixture is heated to 50° C. within 1 hour; this temperature is then maintained for additional 4 hours, during which time yellow suspension of the product is separated. Raney-Ni (4 g) is added to the suspension and, under stirring, hydrazine hydrate (16 ml) is dropwise-added at such a rate that the reaction mixture would be in mild boil. During the reaction, all starting nitrosubstance is dissolved and the reaction mixture bleaches completely. The catalyst is filtered off and thoroughly washed with ethanol. The combined filtrates are concentrated and the concentrated product is dissolved in ethyl acetate (400 ml). Concentrated HCl (20 ml) is added to the solution. The separated hydrochloride is filtered off and thoroughly washed with ethyl acetate. Yield of the product 49 g (80.5%), HPLC 99.0%.

Example 8

Preparation of 1-[2-(2,4-dimethylphenylsulphanyl)phenyl]piperazine 3,5-dinitrobenzoate of Formula I.(DNB)

2-(2,4-Dimethylphenylsulphanyl)benzeneamine hydrochloride of formula XI.HCl (1.5 g; 5.643 mmol) is suspended in the mixture of 45 ml of MTBE and 15 ml of water. Sodium carbonate (1.2 g) is then added and the mixture is stirred at room temperature for 1 hour. The reaction mixture is transferred into a reparatory funnel and thoroughly shaken. After phase separation, the extraction is repeated with 2×15 ml of MTBE. The combined organic phases are washed with 10 ml of water, dried with sodium sulphate and evaporated. bis-(2-Chloroethyl)amine hydrochloride of formula XIIaa, (1.01 g; 5.659 mmol) and NaI (846 mg) are added to the obtained free base dissolved in 15 ml of α,α,α-trifluorotoluene and the reaction mixture is refluxed in an argon atmosphere for 61 hours. A solution of $Na_2CO_3$ (2.1 g) in 20 ml of water is then added at 40° C.; the mixture is cooled down to 20° C. within 30 minutes and then stirred for 1 hour. The free base of vortioxetine is extracted several times with MTBE; the extract is washed with brine (2×) and water (1×) and dried with magnesium sulphate. A solution of 3,5-dinitrobenzoic acid (1.20 g) v 10 ml of boiling EtOAc is added to the concentrated solution of the base. The mixture is heated up to reflux, slowly cooled down to 20° C., stirred at this temperature for 1 hour, and left in a refrigerator overnight. The separated salt is filtered off, washed with ice-cold EtOAc, and dried. 2.05 g of pale yellow crystals were obtained (yield 71%); HPLC purity 98.1%. $^1$H NMR (DMSO-$d_6$, 500 MHz) 8.94 (s, 2H); 8.83 (s, 1H); 7.35 (d, 1H, J=7.81); 7.25 (s, 1H); 7.05-7.20 (m, 3H); 6.92-7.02 (m, 1H); 6.43 (d, 1H, J=7.71); 3.11-3.32 (m, 4H); 2.34 (s, 3H); 2.25 (s, 3H).

Example 9

Preparation of 1-[2-(2,4-dimethylphenylsulphanyl)phenyl]piperazine 3,5-dinitrobenzoate of Formula I.(DNB)

A mixture of 2-(2,4-dimethylphenylsulphanyl)benzeneamine hydrochloride of formula XI. HCl (1.5 g; 5.643 mmol), bis-(2-chloroethyl)amine hydrochloride of formula XIIaa, (1.01 g; 5.659 mmol), NaI (846 mg), $Na_2CO_3$ (3 g), and α,α,α-trifluorotoluene (15 ml) is refluxed in an argon atmosphere for 61 hours. 30 ml of water is then added at 40° C., the mixture is cooled down to 20° C. within 30 minutes and then stirred at this temperature for 1 hour. The free base of vortioxetine is extracted several times with MTBE, the extract is washed with brine (2×) and water (1×), and dried with magnesium sulphate. A solution of 3,5-dinitrobenzoic acid (1.20 g) in 10 ml of boiling EtOAc is added to the concentrated solution of the base. The mixture is heated up to reflux, slowly cooled down to 20° C., stirred at this temperature for 1 hour, and left in a refrigerator overnight. The separated salt is filtered off, washed with ice-cold EtOAc, and dried. 1.74 g of pale yellow crystals were obtained; HPLC purity 95% (yield 60%).

Example 10

Preparation of 1-[2-(2,4-dimethylphenylsulphanyl)phenyl]piperazine 4-chlorobenzoate of Formula I.(PCB)

2-(2,4-Dimethylphenylsulphanyl)benzeneamine hydrochloride of formula XI.HCl (15 g; 56.43 mmol) is suspended in a mixture of 37 ml of toluene and 60 ml of water. After addition of 12 g of sodium carbonate, the mixture is stirred at room temperature for 1 hour. The reaction mixture is poured into a separatory funnel and thoroughly shaken. The separated aqueous phase is extracted 1×18 ml of toluene. The combined organic phases are transferred into a reactor (flask rinsed with 8+5 ml of toluene); bis-(2-chloroethyl)amine hydrochloride (XIIaa, 10.95 g; 61.35 mmol) and KI (7.03 g; 42.325 mmol) are subsequently added and the reaction mixture is refluxed in a nitrogen atmosphere for 30 hours. 90 ml of brine and 18 ml of 30% NaOH are then added at 35° C., the mixture is stirred at the given temperature for 20 minutes, and then left standing at 35° C. overnight. The phases are separated and the aqueous layer is shaken with 2×45 ml of toluene at 35° C. The combined organic phases are washed 2×30 ml of sodium thiosulphate and 2×30 ml of water. 8.44 g of 4-chlorobenzoic acid is then added, the mixture is heated up to reflux, gradually cooled down to 20° C., and left in a refrigerator overnight. The separated vortioxetine 4-chlorobenzoate (I.PCB) is washed with toluene and recrystallized from toluene and subsequently from ethanol. 12.8 g of white crystals were obtained (yield 50%); HPLC purity 99.8%.

Example 11

Preparation of 1-[2-(2,4-dimethylphenylsulphanyl)phenyl]piperazine 4-chlorobenzoate of Formula I.(PCB)

2-(2,4-Dimethylphenylsulphanyl)benzeneamine hydrochloride of formula XI.HCl (15 g, 56.43 mmol) is suspended in a mixture of 37 ml of toluene and 60 ml of water. After adding 12 g of sodium carbonate, the mixture is stirred at room temperature for 1 hour. The reaction mixture is poured into a separatory funnel and shaken thoroughly. The separated aqueous phase is extracted 1×18 ml of toluene. The combined organic phases are transferred into a reactor (flask rinsed with 8+5 ml of toluene), N-Boc-bis(2-chloroethyl)amine of formula XIIba (14.86 g; 61.35 mmol) and KI (7.03 g; 42.325 mmol) are subsequently added, and the reaction mixture is refluxed in the nitrogen atmosphere for 30 hours. 90 ml of brine and 18 ml of 30% NaOH are then added at 35° C., the mixture is stirred at the given temperature for 20 minutes, and then left standing at 35° C. overnight. The phases are separated and the aqueous layer is shaken with 2×45 ml of toluene at 35° C. The combined organic phases are washed with 2×30 ml of sodium thiosulphate and 2×30 ml of water. 8.44 g of 4-chlorobenzoic acid is then added, the mixture is heated up to reflux, gradually cooled down to 20° C., and left in a refrigerator overnight. The separated vortioxetine 4-chlorobenzoate (I.PCB) is washed with toluene, recrystallized from toluene, and subsequently from ethanol. 12.9 g of white crystals are obtained (yield 50%), HPLC purity 99.7%.

Example 12

Preparation of 1-[2-(2,4-dimethylphenylsulphanyl) phenyl]piperazine 4-chlorobenzoate (I.PCB)

2-(2,4-Dimethylphenylsulphanyl)nitrobenzene of formula X, (14.63 g; 56.43 mmol) is placed into an autoclave, 125 ml of methanol and 2.2 g of Ra—Ni are added. The mixture is hydrogenated at pressure of 2000 kPa and temperature of 50° C. for 2 hours. The reaction mixture is cooled down to 20° C., the catalyst is filtered off, and the filtration cake is washed with methanol. Methanol is evaporated and the oily product is co-distilled 3× with toluene. The obtained 2-(2,4-dimethylphenylthio)benzeneamine of formula XI is dissolved in 68 ml of toluene, bis-(2-chloroethyl)amine hydrochloride of formula XIIaa (10.95 g; 61.35 mmol) and KI (7.03 g; 42.325 mmol) are added, and the reaction mixture is refluxed in the nitrogen atmosphere for 30 hours. 90 ml of brine and 18 ml of 30% NaOH are then added at 35° C., the mixture is stirred at this temperature for 20 minutes, and then it is left standing at 35° C. overnight. The phases are separated and the aqueous layer is shaken with 2×45 ml of toluene at 35° C. The combined organic phases are washed with 2×30 ml of sodium thiosulphate and 2×30 ml of water. 8.44 g of 4-chlorobenzoic acid is then added, the mixture is heated up to reflux, gradually cooled down to 20° C., and left in a refrigerator overnight. The separated vortioxetine 4-chlorobenzoate (I.PCB) is washed with toluene, recrystallized from toluene, and subsequently from ethanol. 12.8 g of white crystals are obtained (50%); HPLC purity 99.8%.

Example 13

Preparation of 1-[2-(2,4-dimethylphenylsulphanyl) phenyl]piperazine hydrochloride (I.HCl)

2-(2,4-Dimethylphenylsulphanyl)benzeneamine hydrochloride of formula XI.HCl (1.5 g; 5.643 mmol) was suspended in a mixture of 45 ml of MTBE and 15 ml of water. After adding 1.2 g of sodium carbonate, the mixture is stirred at room temperature for 1 hour. The reaction mixture is poured into a separatory funnel and thoroughly shaken. The phases are separated and the extraction is repeated with 2×15 ml of MTBE. The combined organic phases are washed with 10 ml of water, dried with sodium sulphate, and evaporated. The obtained free base is dissolved in 15 ml of chlorobenzene, 1.01 g (5.643 mmol) of bis-(2-chloroethyl) amine hydrochloride of formula XIIaa is added, and the reaction mixture is refluxed in an argon atmosphere for 72 ours. After cooling down to room temperature, and adding of 50 ml of diethyl ether, the separated product is filtered off. 1.89 g of the title compound is obtained (yield 72%); HPLC purity 90%.

Example 14

Preparation of 1-[2-(2,4-dimethylphenylsulphanyl) phenyl]piperazine of Formula I 2-(2,4-Dimethylphenylsulphanyl)benzeneamine hydrochloride of formula XI.HCl (15 g; 56.43 mmol) is suspended in the mixture of 37 ml of toluene and 60 ml of water. After adding 12 g of sodium carbonate, the mixture is stirred at room temperature for 1 hour. The reaction mixture is poured into a separatory funnel and thoroughly shaken. The separated aqueous phase is extracted with 1×18 ml of toluene. The combined organic phases are transferred into a reactor (flask rinsed with 8+5 ml of toluene), bis-(2-chloroethyl) amine hydrochloride of formula XIIaa (10.95 g; 61.35 mmol) and KI (7.03 g; 42.325 mmol) are subsequently added, and the reaction mixture is refluxed in a nitrogen atmosphere for 30 hours. 90 ml of brine and 18 ml of 30% NaOH are then added at 35° C., the mixture is stirred at this temperature for 20 minutes, and then left standing at 35° C. overnight. The phases are separated and the aqueous layer is shaken in 2×45 ml of toluene at 35° C. The combined organic phases are washed with 2×30 ml of sodium thiosulphate and 2×30 ml of water. After thickening and subsequent crystallization, 9.26 g of the title compound is obtained (yield 55%), HPLC purity 95.0%.

The invention claimed is:

1. A method of preparing 1-(2-(2,4-dimethylphenylsulphanyl)phenyl)piperazine of formula I

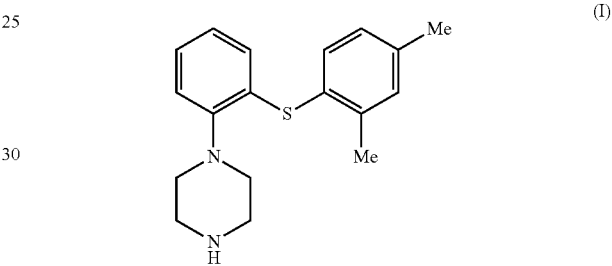

(I)

wherein Me is methyl,
or a salt thereof,
comprising reacting 2-(2,4-dimethylphenylsulphanyl)benzeneamine of formula XI

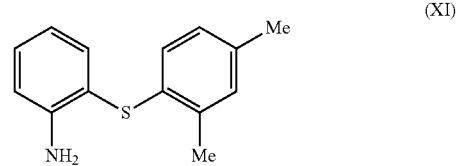

(XI)

wherein Me is methyl,
with a suitable precursor of formation of piperazine ring of formula XII,

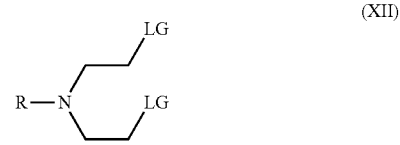

(XII)

wherein LG is a leaving group and R is hydrogen or a protective group,
in a suitable organic solvent.

2. The method according to claim 1, wherein the reaction is carried out without presence of a base in a neutral or acidic environment.

3. The method according to claim 1, wherein the leaving group LG is selected from the group consisting of Cl, Br, I, methylsulfonyloxy, toluenesulfonyloxy, and the protective group is COOR', wherein R' is an unbranched or branched C1-C5 alkyl group.

4. The method according to claim 1, wherein N-unsubstituted derivatives of formula XIIa

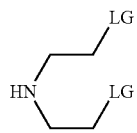     (XIIa)

wherein LG is a leaving group,
are used as precursors of the piperazine nucleus,
or N-protected derivatives of formula XIIb

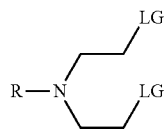     (XIIb)

wherein LG is the leaving group, R is COOR', where R' is an unbranched C1-C5 alkyl group, are used as precursors of the piperazine nucleus.

5. The method according to claim 1, wherein the organic solvent is an aromatic solvent selected from the group consisting of chlorobenzene, xylene, toluene, α,α,α-trifluorotoluene and their mixtures.

6. The method according to claim 1, comprising reacting 2-(2,4-dimethylphenylsulphanyl)benzeneamine of formula XI with 1-1.2 equivalents of bis-(2-chloroethyl)amine hydrochloride in toluene at a temperature of 103-111° C.

7. The method according to claim 1, wherein the amino derivative of formula XI is prepared by reduction of the nitro compound of formula X

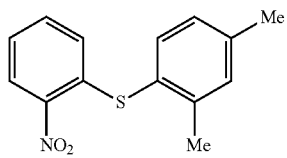     (X)

wherein Me is methyl.

8. The method according to claim 7, wherein the reduction of the nitro compound of formula X is carried out with metals selected from the group consisting of Fe, Zn, and Sn, with metal salts, or by catalytic hydrogenation or transfer-hydrogenation in the presence of a catalyst based on Pt, Pd, Ni, Fe, or Co in a suitable solvent selected from C1-C5 alcohols and esters.

9. The method according to claim 8, wherein the reduction of the nitro compound of formula X is carried out by hydrogenation on Raney-Ni in methanol, ethanol, ethyl acetate, isopropyl acetate, ethyl propionate, or a mixture thereof.

10. The method according to claim 7, wherein the preparation of the nitro compound of formula X comprises reacting the thiol of formula III

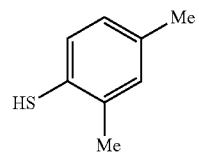     (III)

wherein Me is methyl,
with 2-nitrohalobenzene (IX)

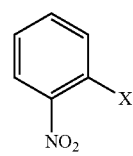     (IX)

wherein X is selected from the group consisting of F, Cl, Br, and I,
in the presence of a base selected from alkali metal alcoholates, alkali hydroxides, and alkali metal carbonates or hydrogen carbonates.

11. The method according to claim 10, comprising reacting the thiol of formula III with 1-chloro-2-nitrobenzene of formula IXb

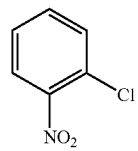     (IXb)

using sodium hydroxide in ethanol.

12. The compound 2-(2,4-dimethylphenylsulphanyl)nitrobenzene of formula X

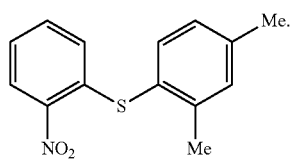     (X)

13. The method according to claim 1, wherein the compound of formula I is further converted to its salt with an acid selected from 3,5-dinitrobenzoic and 4-chlorobenzoic acids.

14. The compound 1-[2-(2,4-Dimethylphenylsulphanyl)phenyl]piperazine 4-chlorobenzoate.

15. The compound 1-[2-(2,4-Dimethylphenylsulphanyl)phenyl]piperazine 3,5-dinitrobenzoate.

16. The method of claim 3, wherein R' is ethoxycarbonyl or butyloxycarbonyl Boc.

17. The method of claim 4, wherein the N-unsubstituted derivative of formula XIIa is bis-(2-chloroethyl)amine or bis-(2-chloroethyl)amine in the form of hydrochloride.

18. The method of claim 4, wherein the N-protected derivative of formula XIIb is N-Boc-bis-(2-chloroethyl) amine.

\* \* \* \* \*